United States Patent [19]

Warriner

[11] Patent Number: Plant 6,443

[45] Date of Patent: Dec. 6, 1988

[54] ROSE PLANT JACYO

[75] Inventor: William A. Warriner, Tustin, Calif.

[73] Assignee: Jackson & Perkins Co., Medford, Oreg.

[21] Appl. No.: 922,631

[22] Filed: Oct. 24, 1986

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Majestic, Gallagher, Parsons & Siebert

[57] ABSTRACT

A hybrid tea rose variety having thick, high substance petals of unusual orange-red color with a pale yellow and orange reverse combined with mildew resistance, outstanding vigor and continual blooming.

1 Drawing Sheet

This present invention relates to a new and distinct variety of rose plant of the hybrid tea class which was originated by crossing an unnamed variety with an unnamed variety.

The primary objective of this breeding was to produce a new rose variety in the hybrid tea class possessing bright orange color, vigor, continual blooming and some disease resistance. This objective was substantially achieved along with other desirable improvements as evidenced by the following unique combination of characteristics which are outstanding in the new variety and which distinguish it from its parents as well as from all other varieties of which I am aware:

1. A bright, orange-red color with a pale reverse;
2. Mildew resistance;
3. Continual blooming;
4. Vigorous upright plant; and
5. Thick petals.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Unnamed variety.

*Pollen parent.*—Unnamed variety.

Classification:

*Botanical.*—Rosa hybrid.

*Commercial.*—Hybrid tea.

FLOWER

Observations made from specimens grown in a greenhouse at Irvine, Calif. in September, 1986.

Blooming habit: Continuous.

Bud:

*Size.*—1½"-2" when petals start to unfurl.

*Form.*—Long, pointed ovoid.

*Color.*—When sepals first divide, red Group 44A at the bud tip, slowly turning to yellow at the base (Yellow Group 10A); when half blown, upper side of petals Red Group 44A; lower side of petals Yellow Group 5C at the petal base to halfway up the petal where it turns to pale orange (Orange Group 32D).

*Sepals.*—Color: Green Group 138A. Three appendaged sepals lightly appendaged. Two unappendaged sepals hairy edged.

*Receptacle.*—Color: Green Group 138A. Shape: Funnel. Size: Medium. Surface: Smooth.

*Peduncle.*—Length: Short. Surface: Smooth, glandular. Color: Medium green. Strength: Stiff.

Open bloom:

*Size.*—Large. Average open size 5".

*Borne.*—Singly.

*Stems.*—Long to medium, strong.

*Form.*—When first open, High center. Permanence: Flattens slightly and outer petals curl back; outer petal edges slightly curled.

*Petalage.*—Number of petals under normal conditions: 24–28.

*Color.*—Center of flower: Upper side of petals, Red Group 44A; reverse side of petals, Yellow Group 5C at the petal base, to halfway up the petal where it turns a pale orange (Orange Group 32D. Base of petals, Yellow Group 10A on upper side, Yellow Group 5C on lower side. Major color: Red Group 44A.

*Variegations.*—None.

*Discoloration.*—General tonality at end of first day: None. Third day: A slight darkening.

*Fragrance.*—Slight.

Petals:

*Texture.*—Thick.

*Shape.*—Obovate.

*Form.*—Tips slightly recurved.

*Arrangement.*—Imbricated. Petaloids in center, few.

*Persistence.*—Drop off cleanly.

*Lastingness.*—On the plant, long. As cut flower, long.

Reproductive parts:

*Anthers.*—Medium. Color: Yellow edged in red. Arrangement: Regular around styles.

*Filaments.*—Color: Reddish brown.

*Pollen.*—Lemon yellow.

*Styles.*—Color: Red.

*Stigmas.*—Color: Greenish white.

PLANT

Form: Bush.

Growth: Vigorous.

Foliage: Number of leaflets on normal mid-stem leaves: 5.

*Size.*—Large.

*Quantity.*—Normal.

*Color.*—New foliage: Reddish. Old foliage: Dark glossy green.

Leaflets:

*Shape.*—Oval pointed.

*Texture.*—Glossy.

*Edge.*—Serrated.

*Serration.*—Single, small.

*Petiole.*—Rachis: Color: Reddish. Underside: Smooth with prickles.

*Stipules.*—Short, smooth with glands.

*Disease resistance.*—Resistant to mildew, under normal growing conditions at Irvine, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked downward.

*Color when young.*—Red.

Small prickles:

*Quantity.*—On main stalks, none. On laterals, none.

I claim:

1. A new and distinct variety of rose plant of the hybrid tea class, substantially as herein shown and described, characterized particularly as to novelty by the unique combination of thick, high substance petals of unusual orange-red color with a pale yellow and orange reverse combined with mildew resistance, outstanding vigor and continual blooming.

* * * * *

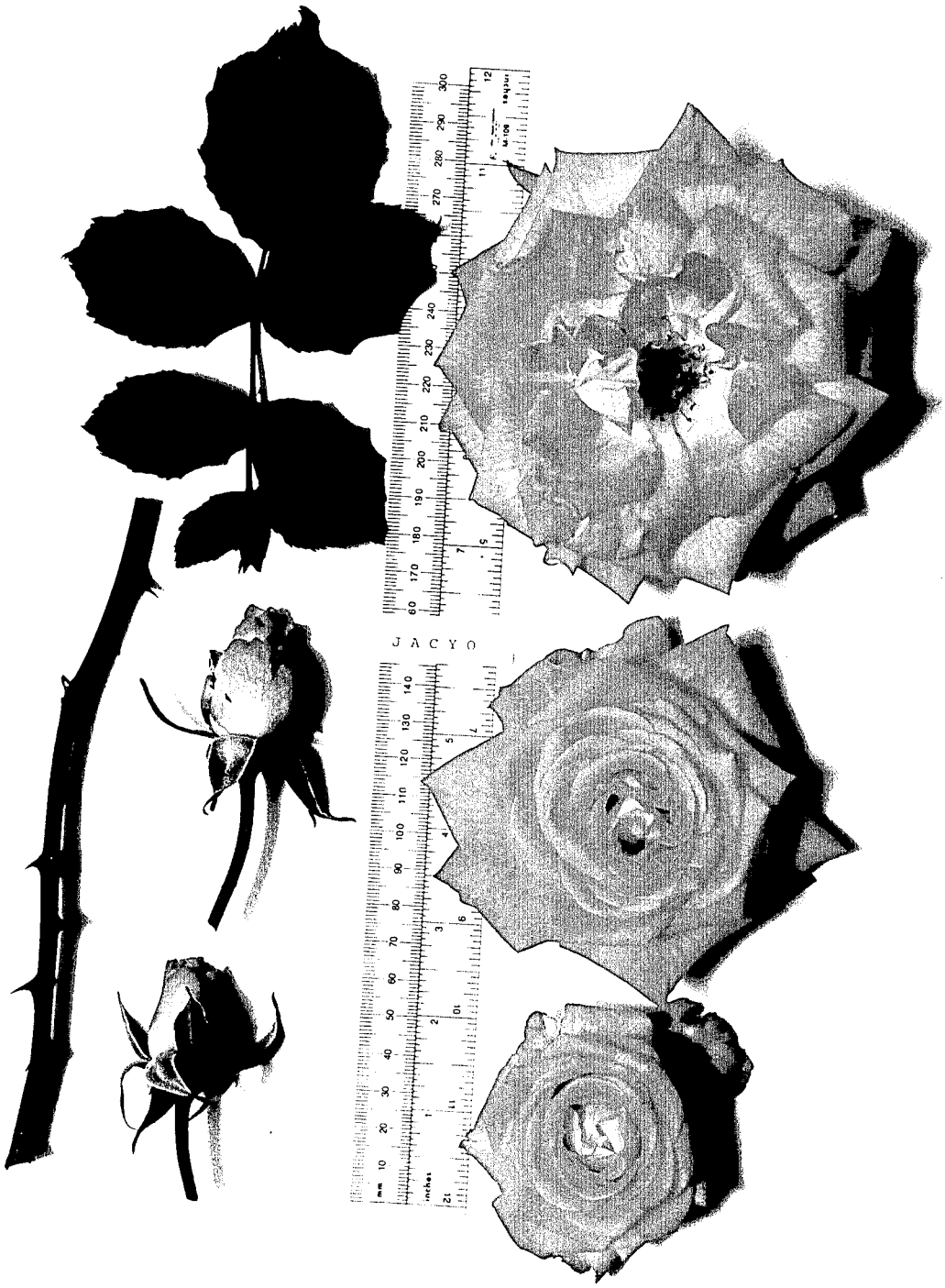
JACYO